US010688252B2

(12) United States Patent
Iwase

(10) Patent No.: US 10,688,252 B2
(45) Date of Patent: Jun. 23, 2020

(54) INJECTION NEEDLE ASSEMBLY AND MEDICINE INJECTION APPARATUS

(71) Applicant: TERUMO KABUSHIKI KAISHA, Tokyo (JP)

(72) Inventor: Yoichiro Iwase, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 98 days.

(21) Appl. No.: 15/716,597

(22) Filed: Sep. 27, 2017

(65) Prior Publication Data

US 2018/0015229 A1 Jan. 18, 2018

Related U.S. Application Data

(63) Continuation of application No. PCT/JP2016/055997, filed on Feb. 29, 2016.

(30) Foreign Application Priority Data

Mar. 27, 2015 (JP) .................................. 2015-065473

(51) Int. Cl.
| A61M 5/32 | (2006.01) |
| A61M 5/50 | (2006.01) |
| A61M 5/46 | (2006.01) |

(52) U.S. Cl.
CPC .......... *A61M 5/3202* (2013.01); *A61M 5/326* (2013.01); *A61M 5/3243* (2013.01);
(Continued)

(58) Field of Classification Search
CPC .. A61M 5/3202; A61M 5/326; A61M 5/3243; A61M 5/46; A61M 5/50; A61M 5/321; A61M 2005/2013; A61M 2005/208
See application file for complete search history.

(56) References Cited

U.S. PATENT DOCUMENTS

| 2010/0292654 | A1 | 11/2010 | Schraga | |
| 2011/0077592 | A1* | 3/2011 | Takemoto | A61M 5/326 604/111 |

(Continued)

FOREIGN PATENT DOCUMENTS

| JP | 2001-137343 | 5/2001 |
| JP | 2010-502316 | 1/2010 |

(Continued)

OTHER PUBLICATIONS

Inernational Search Report issued in International Patent Application No. PCT/JP2016/055997 dated May 17, 2016.
(Continued)

*Primary Examiner* — Bhisma Mehta
*Assistant Examiner* — Nidah M Hussain
(74) *Attorney, Agent, or Firm* — Foley & Lardner LLP

(57) ABSTRACT

An injection needle assembly includes: a needle tube; a needle hub holding the needle tube; a protector movable between a first position at which a needle tip of the needle tube is covered and a second position at which the needle tip of the needle tube is exposed; a biasing member configured to bias the protector toward the needle tip of the needle tube along an axial direction; a retaining member that supports the protector such that the protector is movable along the axial direction, wherein an abutment piece of the protector abuts on the retaining member when the protector is moved to the first position; and a restriction mechanism configured such that, after the protector has moved from the first position to the second position and back to the first position, the restriction mechanism restricts the protector from moving from the first position to the second position again.

6 Claims, 7 Drawing Sheets

(52) U.S. Cl.
CPC ............ *A61M 5/3293* (2013.01); *A61M 5/46* (2013.01); *A61M 5/50* (2013.01); *A61M 2005/3247* (2013.01); *A61M 2005/3267* (2013.01)

(56) References Cited

U.S. PATENT DOCUMENTS

| | | | |
|---|---|---|---|
| 2012/0046615 A1* | 2/2012 | Koiwai | A61M 5/46 604/192 |
| 2013/0096502 A1 | 4/2013 | Kawamoto et al. | |
| 2016/0022924 A1 | 1/2016 | Iwase et al. | |

FOREIGN PATENT DOCUMENTS

| | | |
|---|---|---|
| JP | 2015-039630 | 3/2015 |
| WO | WO-2009/114762 | 9/2009 |
| WO | WO-2009/119770 | 10/2009 |
| WO | WO-2010/103950 | 9/2010 |
| WO | WO-2010/116832 | 10/2010 |
| WO | WO-2014/162583 A1 | 10/2014 |

OTHER PUBLICATIONS

Extended European Search Report dated Nov. 13, 2018 in corresponding application No. 16772025.9.

\* cited by examiner

INJECTION NEEDLE ASSEMBLY AND MEDICINE INJECTION APPARATUS

CROSS-REFERENCE TO RELATED APPLICATIONS

The present application in a bypass continuation of PCT Application No. PCT/JP2016/055997, filed on Feb. 29, 2016, which claims priority to Japanese Application No. 2015-065473, filed on Mar. 27, 2015. The contents of these applications are hereby incorporated by reference in their entireties.

BACKGROUND

The present application relates to an injection needle assembly and a medicine injection apparatus which are used to puncture a surface of skin with a needle tip and inject a medicine into a skin upper layer portion.

BACKGROUND ART

In recent years, human infection with avian influenza has been reported, and there are growing concerns about damage due to an outbreak (pandemic) of infection from individual to individual. For this reason, pre-pandemic vaccines which can be effective for avian influenza have been stockpiled all over the world. In addition, in order to administer pre-pandemic vaccines to many humans, a study for increasing the production volume of the vaccines has been conducted.

The skin includes three portions: the epidermis, the dermis, and the subcutaneous tissue. The epidermis is a layer of about 50 to 200 µm from a skin surface, and the dermis is a layer of about 1.5 to 3.5 mm continuing from the epidermis. Because influenza vaccine is generally administered subcutaneously or intramuscularly, the vaccine is administered to a lower layer of the skin or a part deeper than the lower layer.

It has been reported that even when a dosage amount is reduced by administration of the influenza vaccine to a target region which is a skin upper layer portion where many immunocytes are present, an immunity acquiring ability equivalent to that of hypodermic or intramuscular administration is obtained. Thus, because the dosage amount can be reduced by administration of the pre-pandemic vaccine to the skin upper layer portion (i.e., the epidermis and the dermis of the skin), the pre-pandemic vaccine can be administered to more individuals.

Various methods using a single needle, multiple needles, a patch, gas, etc. have been reported as methods for administering a medicine to the skin upper layer portion. Considering administration stability, reliability, and a manufacturing cost, the method using the single needle is most suitable as the method for administration to the skin upper layer portion. A Mantoux's test is known as a method for administering a vaccine to the skin upper layer portion by means of the single needle. The Mantoux's test is generally a method for administering a medicine of about 100 µl in such a manner that a needle having a short bevel needle tip with a size of 26 to 27 gauge is, from a diagonal direction of about 10 to 15°, inserted into the skin by about 2 to 5 mm.

However, it is difficult to perform the technique of the Mantoux's test for medicine administration, and for this reason, the success rate of the Mantoux's test depends on the skill of a doctor who performs the injection. There is a probability that an individual, especially a child, moves during administration, and for this reason, it is difficult to administer the influenza vaccine by the Mantoux's test. Thus, there is a demand for development of a device configured to easily administer a vaccine to the skin upper layer portion.

JP 2001-137343 A describes an injection apparatus for a skin upper layer portion in which a limiter having a skin contact surface is connected to a needle hub. The limiter described in JP 2001-137343 A is provided around a needle tube and has a gap against the needle tube. A medicine is administered into the skin by restricting a length (protrusion length) of the needle tube protruding from a surface of the limiter contacting the skin to 0.5 to 3.0 mm.

SUMMARY

In the injection apparatus described in JP 2001-137343 A, however, a needle distal end portion of the needle tube always protrudes from the surface of the limiter contacting the skin, and thus, there is a possibility that a needle tip of the needle tube may erroneously puncture a user after administration of the medicine or at the time of disposal of the medicine injection apparatus, which is problematic.

An object of certain embodiments of the present invention is to provide an injection needle assembly and a medicine injection apparatus capable of inhibiting a needle tip of a needle tube from erroneously puncturing a user after administration of a medicine or at the time of disposal.

In one embodiment, an injection needle assembly includes: a needle tube having a needle tip capable of puncturing a living body; a needle hub which holds the needle tube; a protector; a biasing member; a retaining member; and a restriction mechanism. The protector is movable to a first position to cover the needle tip of the needle tube and a second position to expose the needle tip of the needle tube. The biasing member biases the protector toward the needle tip side of the needle tube along an axial direction of the needle tube. The retaining member supports the protector so as to be movable along the axial direction of the needle tube, and an abutment piece provided on the protector abuts on the retaining member when the protector is moved to the first position. The restriction mechanism restricts the protector from moving again from the first position to the second position after the protector moves from the first position to the second position and further moves from the second position to the first position.

In another embodiment, a medicine injection apparatus includes: the above-described injection needle assembly; and a syringe that is detachably attached to the injection needle assembly.

According to certain embodiments of the injection needle assembly and the medicine injection apparatus, it is possible to inhibit the needle tip of the needle tube after use from puncturing against an intention of the user.

DETAILED DESCRIPTION

Hereinafter, embodiments of an injection needle assembly and a medicine injection apparatus will be described with reference to FIGS. 1 to 7. Common members are denoted by identical reference signs throughout the drawings. the present invention is not limited to the following embodiments.

The description will be given in the following order.
1. First Embodiment
1-1. Configuration Examples of Injection Needle Assembly and Medicine Injection apparatus
1-2. How to Use Medicine Injection apparatus
2. Second Embodiment 1. First Embodiment 1-1. Configuration Examples of Injection Needle Assembly and Medicine Injection Apparatus First, an injection needle assembly and a medicine injection apparatus according to a first embodiment (hereinafter, referred to as the "present embodiment") of the present invention will be described with reference to FIGS. 1 and 2.

Figure 1:
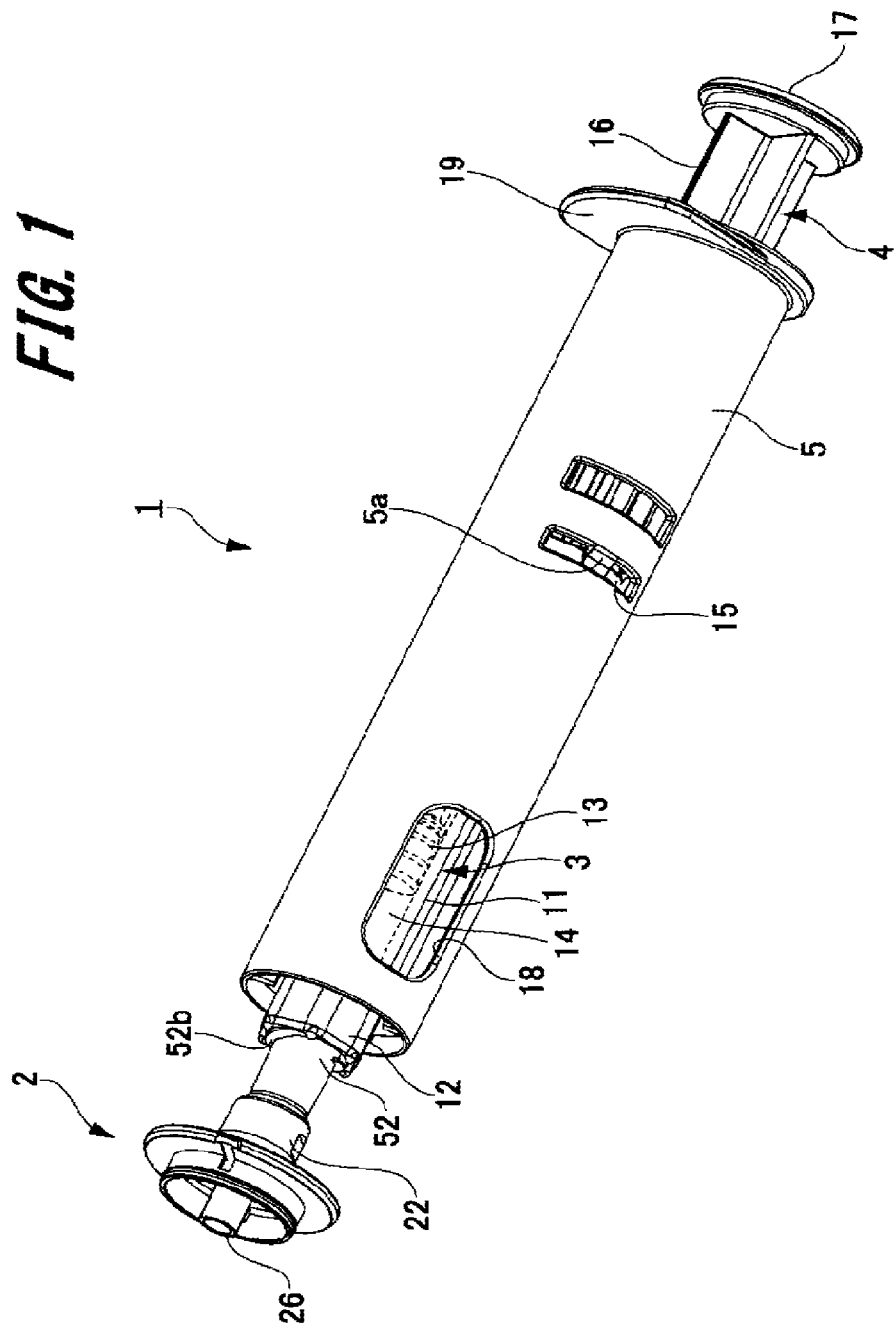
FIG. 1 is a perspective view illustrating a medicine injection apparatus according to a first embodiment of the present invention.
Figure 2:
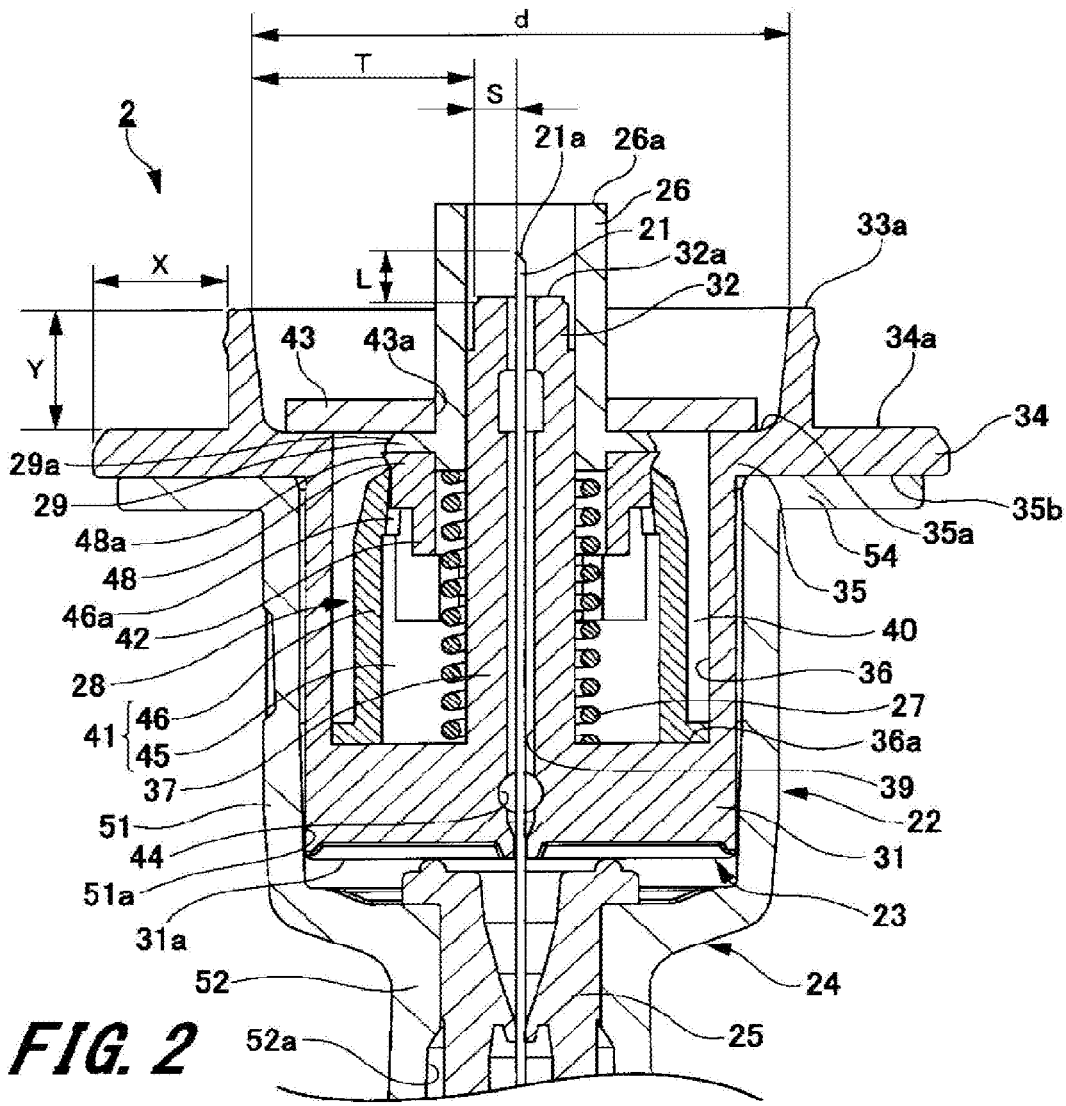
FIG. 2 is a cross-sectional view illustrating the medicine injection apparatus according to the first embodiment of the present invention.

FIG. 1 is a perspective view illustrating the medicine injection apparatus of the present embodiment, and FIG. 2 is a sectional view illustrating the injection needle assembly of the present embodiment.

A medicine injection apparatus 1 is used in the case of puncturing a surface of skin with a needle tip and injecting a medicine into a skin upper layer portion. As illustrated in FIG. 1, the medicine injection apparatus 1 includes an injection needle assembly 2, a syringe 3 that is detachably attached to the injection needle assembly 2, a pusher member 4, and a syringe holder 5 that holds the syringe 3.

[Syringe]

The syringe 3 is a pre-filled syringe that is filled with a medicine in advance. The syringe 3 has a syringe main body 11, a discharge part formed at first end portion in an axial direction of the syringe main body 11, a lock mechanism 12 provided in the discharge part, and a gasket 13.

The syringe main body 11 is formed in a substantially cylindrical shape with a hollow. In addition, the gasket 13 is disposed slidably in a cylindrical hole of the syringe main body 11. The gasket 13 is formed in a substantially columnar shape and is in liquid-tight close contact with an inner peripheral surface of the cylindrical hole of the syringe main body 11. Further, the gasket 13 partitions an internal space of the syringe main body 11 into two. A space closer to the discharge part side than the gasket 13 in the syringe main body 11 serves as a liquid chamber 14 that is filled with the medicine. On the other hand, a plunger main body 16 of the pusher member 4, which will be described later, is inserted into a space closer to the second end side than the gasket 13 in the syringe main body 11.

A material of the gasket 13 is not particularly limited, but it is preferable to use an elastic material in order to obtain favorable liquid tightness with the syringe main body 11. Examples of the elastic material may include various rubber materials, such as natural rubber, isobutylene rubber, and silicone rubber, various thermoplastic elastomers, such as an olefin type and a styrene type, or mixtures thereof.

An outer diameter and an inner diameter of the syringe main body 11 are appropriately set according to the use of the medicine injection apparatus 1 and the volume of the medicine to be contained in the liquid chamber 14. For example, when the volume of the medicine to be contained is set to 0.5 mL using a general-purpose high-speed filling machine, it is preferable to set the inner diameter of the syringe main body 11 to 4.4 to 5.0 mm and the outer diameter of the syringe main body 11 to 6.5 to 8.4 mm. In addition, when the volume is set to 1 mL, it is preferable to set the inner diameter of the syringe main body 11 to 6.1 to 9.0 mm and the outer diameter of the syringe main body 11 to 7.9 to 12.5 mm.

Examples of the medicine may include various vaccines to inhibit various infectious diseases, such as influenza, but the medicine is not limited to the vaccine. Examples of medicines other than the vaccine may include a sugar injection solution like glucose, an injection solution for correction of electrolyte, such as sodium chloride or potassium lactate, vitamins, antibiotic infusion solutions, contrast media, steroids, protease inhibitors, fat emulsions, anticancer agents, anesthetic, heparin calcium, antibody preparations, and the like.

A flange part 15 is formed at the second end portion in the axial direction of the syringe main body 11. The flange part 15 is engaged with an engaging part 5a provided in the syringe holder 5 to be described later. In addition, the discharge part (not illustrated) is continuously formed at first end portion in the axial direction of the syringe main body 11.

The discharge part is formed in a substantially cylindrical shape to be coaxial with the syringe main body 11. In addition, a cylindrical hole of the discharge part communicates with the cylindrical hole of the syringe main body 11. The discharge part is formed in a tapered shape whose diameter continuously decreases toward the first end portion in the axial direction. When the injection needle assembly 2 is attached to the syringe 3, a distal end portion of the discharge part is in liquid-tight close contact with an end face of an elastic member 25 of the injection needle assembly 2 to be described later.

The lock mechanism 12 is provided in the discharge part. The lock mechanism 12 is a luer lock part representing an example of a fixing mechanism. The lock mechanism 12 is formed in a tubular shape that coaxially surrounds the discharge part. In addition, the lock mechanism 12 has a circular inner periphery, and an outer periphery thereof is formed in a hexagonal shape. A female screw part is formed on an inner peripheral surface of the lock mechanism 12. The female screw part is formed so as to be screwable with a male screw part 52b provided in the injection needle assembly 2.

Examples of a material of the syringe main body 11 may include various types of resin such as polyvinyl chloride, polyethylene, polypropylene, cyclic polyolefin, polystyrene, poly-(4-methylpentene-1), polycarbonate, acrylic resin, an acrylonitrile-butadiene-styrene copolymer, polyester such as polyethylene terephthalate, a butadiene-styrene copolymer, and polyamide (for example, nylon 6, nylon 6/6, nylon 6/10, and nylon 12). Among them, it is preferable to use resin such as polypropylene, cyclic polyolefin, polyester, and poly-(4-methylpentene-1) from the viewpoint that molding is easy. Incidentally, it is preferable that the material of the syringe main body 11 be substantially transparent in order to secure the visibility of the interior.

Although the example in which the pre-filled syringe, filled with the medicine in advance, is applied as the syringe 3 has been described in the present embodiment, the present invention is not limited thereto, and a syringe in which the inside of a syringe main body is not filled with a medicine in advance may be applied.

[Pusher Member]

The pusher member 4 has the plunger main body 16 and an operation part 17 to operate the plunger main body 16. The plunger main body 16 is formed in a rod shape. The plunger main body 16 is inserted into the cylindrical hole of the syringe main body 11 from an opening portion formed at the second end portion in the axial direction of the syringe main body 11. Further, first end portion in an axial direction of the plunger main body 16 abuts on the gasket 13.

The operation part 17 is formed at the second end portion in the axial direction of the plunger main body 16. The operation part 17 is formed in a substantially disc shape. When using the medicine injection apparatus 1, the operation part 17 is pressed by a user. As a result, the first end portion in the axial direction of the plunger main body 16 abuts on the gasket 13 to cause the gasket 13 to slide toward the discharge part.

In addition, various types of resin exemplified as the material of the syringe main body 11 can be applied as a material of the pusher member 4.

[Syringe Holder]

Next, the syringe holder 5 will be described.

The syringe holder 5 is formed in a substantially cylindrical shape. The syringe holder 5 covers an outer peripheral surface of the syringe main body 11 and an outer peripheral surface of the lock mechanism 12 in the syringe 3. The syringe holder 5 is configured to enable grip of the user at the time of attaching the injection needle assembly 2 to the syringe 3.

A viewing window 18 is formed at first end portion in an axial direction of the syringe holder 5. The viewing window 18 is provided at a position where the liquid chamber 14 of the syringe 3 is visible from the outside of the syringe holder 5 when the syringe 3 is attached to the syringe holder 5. Accordingly, it is possible to secure the visibility of the interior even if the syringe holder 5 is attached to the syringe 3.

In addition, the holder flange 19 is formed at the second end in the axial direction of the syringe holder 5. The holder flange 19 protrudes to be substantially perpendicular to apart of the outer peripheral surface of the syringe holder 5. Since the holder flange 19 is provided, it is possible to inhibit a finger gripping the syringe holder 5 from slipping toward the second end portion in the axial direction when the user grips the syringe holder 5 and administers the medicine. In addition, it is possible to inhibit the medicine injection apparatus 1 from rolling when placing the medicine injection apparatus 1 on a desk, a table, or the like.

Further, the engaging part 5a is provided in a middle portion in the axial direction of the syringe holder 5. The engaging part 5a is an opening portion that passes through an outer wall of the syringe holder 5. The flange part 15 of the syringe 3 is engaged with the engaging part 5a.

It is possible to increase a diameter of the medicine injection apparatus 1 by attaching the syringe holder 5 to the syringe 3 so that it is easy to grip the medicine injection apparatus 1. As a result, the operability at the time of operating the pusher member 4 is improved.

[Injection Needle Assembly]

Next, the injection needle assembly 2 will be described.

As illustrated in FIGS. 1 and 2, the injection needle assembly 2 includes a hollow needle tube 21 and a needle hub 22 which holds the needle tube 21.

[Needle Tube]

As illustrated in FIG. 2, a needle tube having a size (0.2 to 0.45 mm in outside diameter) conforming to 26- to 33-gauge according to ISO medical needle tube standard (ISO9626:1991/Amd. 1:2001(E)) is used as the needle tube 21, and preferably, a needle tube having a size of 30- to 33-gauge is used. Incidentally, a needle smaller than 33-gauge may be used.

A needle tip 21a having a blade surface is provided at a first end of the needle tube 21. Hereinafter, the second end of the needle tube 21 on the opposite side to the needle tip 21a will be referred to as a "proximal end". A length in the axial direction of the needle tube 21 on the blade surface (hereinafter, referred to as a "bevel length") is preferably 1.4 mm (adults) or less, which is a minimum thickness of the skin upper layer portion to be described later, and is preferably about 0.5 mm or more which is a bevel length in the case where a short bevel is formed in the needle tube of 33-gauge. That is, the bevel length is preferably set in a range of 0.5 to 1.4 mm.

Further, the bevel length is more preferable if the minimum thickness of the skin upper layer portion is 0.9 mm (children) or less, that is, the bevel length is in a range of 0.5 to 0.9 mm. Incidentally, the short bevel indicates a blade surface formed at an angle of 18 to 25° relative to a longitudinal direction of the needle that is commonly used for an injection needle.

For example, stainless steel can be exemplified as a material of the needle tube 21, but the material is not limited thereto, and it is possible to use aluminum, an aluminum alloy, titanium, a titanium alloy, and other metals. In addition, not only a straight needle but also a tapered needle having at least a part formed in a tapered shape can be used as the needle tube 21. The tapered needle may be obtained by forming a proximal end portion to have a larger diameter than a distal end portion of the needle and an intermediate portion thereof to have a tapered structure. In addition, a sectional shape of the needle tube 21 may be not only a circular shape but also a polygonal shape such as a triangle.

[Needle Hub]

The needle hub 22 includes a first member 23 which holds the needle tube 21, a second member 24 into which the discharge part of the syringe 3 is fitted, the elastic member 25, a protector 26, a biasing member 27, a restriction mechanism 28. The first member 23 and the second member 24 are formed as separate members. Examples of materials of the first member 23 and the second member 24 may include synthetic resin such as polycarbonate, polypropylene, and polyethylene.

The first member 23 includes a base part 31, an adjustment part 32, a stabilization part 33, a guide part 34, and a support part 37. The base part 31 is formed in a substantially columnar shape. A housing recess 36 is formed in the base part 31. The housing recess 36 is formed to be recessed in a substantially columnar shape from a first end to a second end in an axial direction of the base part 31. Further, the entire first end face in the axial direction of the base part 31 is opened. The support part 37 is provided in the housing recess 36.

The support part 37 is provided at a central portion of a bottom surface 36a of the housing recess 36 and protrudes from the bottom surface 36a of the housing recess 36 toward the one side in the axial direction of the base part 31. The support part 37 is formed in a substantially columnar shape.

In addition, the adjustment part 32 is continuously provided on a first end face in an axial direction of the support part 37. The adjustment part 32 is a columnar protruding part that protrudes in the axial direction of the support part 37. An axial center of the adjustment part 32 coincides with each axis of the base part 31 and the support part 37.

A through hole 39 through which the needle tube 21 passes is provided in the axial centers of the base part 31, the support part 37, and the adjustment part 32. The base part 31 is provided with an injection hole 44 configured to inject an adhesive material into the through hole 39. The injection hole 44 is opened to the outer peripheral surface of the base part 31 closer to the other side in the axial direction than the housing recess 36, and communicates with the through hole 39. That is, the needle tube 21 is fixed to the base part 31 and the support part by the adhesive material injected from the injection hole 44 into the through hole 39.

The proximal end side of the needle tube 21 protrudes from an end face 31a of the base part 31 on the other side in the axial direction. The base part 31 is inserted into the second member 24 from the end face 31a, and the proximal end side of the needle tube 21 is inserted into an insertion hole of the elastic member 25. Further, the end face 31a of the base part 31 abuts on an end face of the elastic member 25.

In addition, a connection piece 35 is provided on the outer peripheral surface of the base part 31. The connection piece 35 is formed as a ring-shaped flange part that protrudes outward in a radial direction of the base part 31 on a first end side in the axial direction of the base part 31. The connection piece 35 has flat surfaces 35a and 35b opposing each other in the axial direction of the base part 31. The second member 24 is connected to the flat surface 35b of the connection piece 35. In addition, a distal end portion of the connection piece 35 forms the guide part 34. The guide part 34 will be described later in detail.

The end face of the adjustment part 32 forms a needle protrusion surface 32a on which the needle tip 21a side of the needle tube 21 protrudes. The needle protrusion surface 32a is formed as a flat surface orthogonal to the axial direction of the needle tube 21. This needle protrusion surface 32a defines a depth of puncture of the needle tube 21 in contact with the surface of the skin when puncturing the skin upper layer portion with the needle tube 21. That is, the depth of puncture of the needle tube 21 in the skin upper layer portion is determined by a length (hereinafter, referred to as a "protrusion length L") of the needle tube 21 protruding from the needle protrusion surface 32a (see FIG. 3).

A thickness of the skin upper layer portion corresponds to a depth from the surface of the skin to a dermis layer and is generally in a range of 0.5 to 3.0 mm. Thus, the protrusion length L of the needle tube 21 can be set within the range of 0.5 to 3.0 mm.

Meanwhile, an administration site of an influenza vaccine is generally the deltoid muscle. In view of this, the thickness of the skin upper layer portion at the deltoid muscle was measured for 19 infants and 31 adults. The measurement was conducted by imaging the skin upper layer portion where ultrasonic reflectance is high using an ultrasonic measuring instrument (NP60R-UBM, a high-resolution echo system for small animals, manufactured by NEPA GENE CO., LTD.). Incidentally, measurement values were in log-normal distribution so that a range of MEAN±2SD was obtained by a geometric mean.

As a result, the thickness of the skin upper layer portion at the deltoid muscle of children was 0.9 to 1.6 mm. In addition, the thickness of the skin upper layer portion at the deltoid muscle of adults was 1.4 to 2.6 mm in a distal region, 1.4 to 2.5 mm in a central region, and 1.5 to 2.5 mm in a proximal region. From the above, it was confirmed that the thickness of the skin upper layer portion at the deltoid muscle is 0.9 mm or more in the case of children, and 1.4 mm or more in the case of adults. Therefore, it is preferable to set the protrusion length L of the needle tube 21 in a range of 0.9 to 1.4 mm at the time of injection into the skin upper layer portion at the deltoid muscle.

When the protrusion length L is set as described above, it is possible to position the blade surface of the needle tip 21a in the skin upper layer portion. As a result, a needle hole (medicine discharge port) opening to the blade surface is positioned in the skin upper layer portion at any position in the blade surface. Even if the medicine discharge port is positioned in the skin upper layer portion, the medicine flows into a subcutaneous tissue from a portion between a side surface of the end portion of the needle tip 21a and the incised skin when the needle tip 21a is stuck to be deeper than the skin upper layer portion, and thus, it is important that the blade surface is reliably present in the skin upper layer portion.

It is difficult to set the bevel length to be 1.0 mm or less with a needle tube larger than 26-gauge in the case of being used for administration to the skin upper layer portion. Therefore, it is preferable to use a needle tube narrower than 26-gauge in order to set the protrusion length L of the needle tube 21 to the preferable range (0.9 to 1.4 mm).

The needle protrusion surface 32a of the adjustment part 32 is formed such that a distance S from a peripheral edge to the outer peripheral surface of the needle tube 21 is 1.4 mm or less, and is preferably formed in a range of 0.3 to 1.4 mm. The distance S from the peripheral edge of the needle protrusion surface 32a to the peripheral surface of the needle tube 21 is set upon considering that pressure is applied to a blister formed by administering the medicine to the skin upper layer portion. That is, the needle protrusion surface 32a is set to a size that is sufficiently smaller than the blister formed in the skin upper layer portion and does not to hinder the formation of the blister. As a result, it is possible to inhibit the administered medicine from leaking even if the needle protrusion surface 32a presses the skin around the needle tube 21.

The stabilization part 33 is formed in a tubular shape protruding from the flat surface 35a of the connection piece 35. The needle tube 21, the adjustment part 32, and the protector 26, which will be described later, are disposed in a cylindrical hole of the stabilization part 33. That is, the stabilization part 33 is formed in the tubular shape to cover the adjustment part 32 through which the needle tube 21 passes and the periphery of the protector 26, and is provided to be spaced part from the needle tip 21a of the needle tube 21 in the radial direction.

An end face 33a of the stabilization part 33 is positioned closer to the proximal end side of the needle tube 21 than the needle protrusion surface 32a of the adjustment part 32. When the living body is punctured with the needle tip 21a of the needle tube 21, the needle protrusion surface 32a first comes into contact with the surface of the skin, and then, the end face 33a of the stabilization part 33 comes into contact with the surface of the skin. At this time, the medicine injection apparatus 1 is stabilized as the end face 33a of the stabilization part 33 comes into contact with the skin, and it is possible to maintain the needle tube 21 in a posture that is substantially perpendicular to the skin.

Incidentally, it is possible to maintain the needle tube 21 in the posture that is substantially perpendicular to the skin even if the end face 33a of the stabilization part 33 is positioned on the same plane as the needle protrusion surface 32a or positioned to be closer to the needle tip 21a side of the needle tube 21 than the needle protrusion surface 32a. When considering the swell of the skin when the stabilization part 33 is pushed to the skin, a distance in the axial distance between the end face 33a of the stabilization part 33 and the needle protrusion surface 32a is preferably set to 1.3 mm or less.

In addition, an inner diameter d of the stabilization part 33 is set to a value which is equal to or larger than a diameter of the blister formed on the skin. Specifically, a distance T from an inner wall surface of the stabilization part 33 to the peripheral edge of the needle protrusion surface 32a is set to be in a range of 4 mm to 15 mm. Accordingly, no pressure is applied to the blister from the inner wall surface of the stabilization part 33, and it is possible to inhibit the blister formation from being hindered.

The distance T from the inner wall surface of the stabilization part 33 to the needle protrusion surface 32a is not particularly limited as long as being 4 mm or more. However, an outer diameter of the stabilization part 33 increases when the distance T increases, and it is difficult to bring the entire end face 33a of the stabilization part 33 into contact with the skin in the case of puncturing a narrow arm of a child with the needle tube 21. Thus, it is preferable that the maximum of the distance T be defined as 15 mm in consideration of the narrowness of the arm of the child.

If the distance S from the needle protrusion surface 32a to the outer peripheral surface of the needle tube 21 is 0.3 mm or more, the adjustment part 32 does not enter the skin. Therefore, it is possible to set the inner diameter d of the stabilization part 33 to 9 mm or more when considering the distance T (4 mm or more) from the inner wall surface of the stabilization part 33 to the peripheral edge of the needle protrusion surface 32a and the diameter (about 0.3 mm) of the needle protrusion surface 32a.

Incidentally, the shape of the stabilization part 33 is not limited to the cylindrical shape, and may be formed in a square tubular shape, such as a quadrangular prism and a hexagonal prism, having a cylindrical hole in the center, for example.

The guide part 34 is a portion on the distal end side that is positioned outward in the radial direction of the first member 23 of the stabilization part 33 in the connection piece 35. The guide part 34 has a contact surface 34a which comes into contact with the skin. The contact surface 34a is a part of the flat surface 35a of the connection piece 35 and is a flat surface that is substantially parallel to the end face 33a of the stabilization part 33. It is possible to constantly secure the force pressing the skin of the stabilization part 33 and the needle tube 21 at a predetermined value or more by pushing the stabilization part 33 until the contact surface 34a of the guide part 34 comes into contact with the skin. Accordingly, a portion (corresponding to the protrusion length L) of the needle tube 21 that protrudes from the needle protrusion surface 32a is reliably stuck into the skin.

A length of a distance (hereinafter, referred to as "guide part height") Y from the contact surface 34a of the guide part 34 to the end face 33a of the stabilization part 33 is set such that the needle tube 21 and the stabilization part 33 can press and puncture the skin with an appropriate pressing force.

Incidentally, the appropriate pressing force of the needle tube 21 and the stabilization part 33 is, for example, 3 to 20 N. Accordingly, the guide part 34 guides the pressing force, generated by the needle tube 21 and the stabilization part 33, to the skin, and it is possible to reliably position the needle tip 21a of the needle tube 21 in the skin upper layer portion and to grant the user a sense of security.

The guide part height Y is appropriately determined based on the inner diameter d of the stabilization part 33 and a length (hereinafter, referred to as a "guide part length") X from a distal end face of the guide part 34 to the outer peripheral surface of the stabilization part 33. For example, when the inner diameter d of the stabilization part 33 is 12 mm and the guide part length X is 3.0 mm, the guide part height Y is set in a range of 2.3 to 6.6 mm.

Next, the protector 26 will be described. As illustrated in FIG. 1 and FIG. 2, the protector 26 covers the adjustment part 32 through which the needle tube 21 passes and the periphery of the needle tip 21a of the needle tube 21 in the state before puncturing the skin with the needle tube 21.

In addition, the protector 26 is formed in a cylindrical shape. The protector 26 is supported by the support part 37 and the retaining member 43 so as to be movable in axial directions thereof (the axial direction of the needle tube 21). Further, a part of the other side in the axial direction of the protector 26 is inserted into a space 40 that is formed between the housing recess 36 and the support part 37.

It is preferable to set a wall thickness of the protector 26 to be sufficiently smaller than the diameter of the needle protrusion surface 32a in order to inhibit the formation of the blister from being hindered.

An abutment piece 29 is provided on a side of the protector 26 opposite to the needle tip 21a of the needle tube 21, that is, the second end side in the axial direction. The abutment piece 29 is formed as a ring-shaped flange part protruding outward in the radial direction from an outer peripheral surface of the protector 26. In addition, an inclined surface 29a is provided at an outer edge on the outer side in the radial direction of the abutment piece 29. The inclined surface 29a is provided at a corner portion of the outer edge of the abutment piece 29 on the needle tip 21a side of the needle tube 21. The inclined surface 29a is formed into a tapered shape whose diameter continuously decreases from the other side to the one side in the axial direction.

In addition, an engagement member 41 and an extension member 42 of the restriction mechanism 28, which will be described later, are disposed on the other side in the axial direction of the protector 26.

The shape of the protector 26 is not limited to the cylindrical shape, but may be formed into a square tubular shape, such as a quadrangular prism and a hexagonal prism, having a cylindrical hole in the center, for example.

The biasing member 27 is disposed in the space 40 formed in the housing recess 36 and is interposed between the second end face in the axial direction of the protector 26 and the bottom surface 36a of the housing recess 36. Further, the biasing member 27 is disposed so as to cover the periphery of the outer peripheral surface of the support part 37.

The biasing member 27 is a compression coil spring and biases the protector 26 toward the one side in the axial direction, that is, the needle tip 21a side of the needle tube 21. A biasing force of the biasing member 27 is set to be smaller than the appropriate pressing force at the time of puncturing the skin with the needle tube 21, and is set to, for example, 3 N or less. Accordingly, the biasing force of the biasing member 27 does not hinder the positioning of the needle tip 21*a* of the needle tube 21 in the skin upper layer portion at the time of puncturing the skin with the needle tube 21, and thus, it is possible to reliably position the needle tip 21*a* of the needle tube 21 in the skin upper layer portion.

Although the example in which the compression coil spring is applied as the biasing member 27 has been described in the present embodiment, the present invention is not limited thereto. The biasing member may be any elastic member that elastically deforms when a predetermined pressing force is applied, and it is possible to apply, for example, other various spring members such as a leaf spring, a sponge, a gel, and a rubber member.

Next, the restriction mechanism 28 will be described. The restriction mechanism 28 has the engagement member 41 and the extension member 42. The engagement member 41 has a cylindrical part 45 formed in a substantially cylindrical shape and a plurality of engaging parts 46.

The engagement member 41 is disposed in the housing recess 36. Further, the cylindrical part 45 is fixed to the bottom surface 36*a* of the housing recess 36. Further, the engagement member 41 is disposed so as to cover the periphery of the other side of the support part 37 in the axial direction. The plurality of engaging parts 46 are continuously formed on one side in an axial direction of the cylindrical part 45.

The plurality of engaging parts 46 are provided on a first end face in the axial direction of the cylindrical part 45 at a predetermined interval along a circumferential direction thereof. The plurality of engaging parts 46 protrude in a substantially flat plate shape from the first end face in the axial direction of the cylindrical part 45. In addition, the plurality of engaging parts 46 are formed in a tongue shape and are provided with elasticity.

A distal end portion of the engaging part 46 is inclined with respect to the axial direction of the needle tube 21 so as to approach the inner side in the radial direction than a proximal end portion on the cylindrical part 45 side, that is, the support part 37. An engagement piece 46*a* is provided on a surface on the inner side in the radial direction of the distal end portion of the plurality of engaging parts 46. The engagement piece 46*a* protrudes to be substantially perpendicular to the inner side in the radial direction from the surface on the inner side of the engaging part 46.

In addition, a diameter of a space, formed by the plurality of engaging parts 46 when the plurality of engaging parts 46 are in a natural state without being elastically deformed, is set to be slightly smaller than an outer diameter of the abutment piece 29 of the protector 26. Further, the extension member 42 is disposed between the plurality of engaging parts 46 of the engagement member 41.

The extension member 42 is formed in a substantially cylindrical shape. The extension member 42 is detachably attached to an outer peripheral portion of the protector 26 on the other side in the axial direction with respect to the abutment piece 29. An extension part 48 is provided on one side in an axial direction of the extension member 42.

The extension part 48 overhangs outward in the radial direction from an outer peripheral surface of the extension member 42. First end portion in an axial direction of the extension part 48 has an outer diameter continuously increasing from the other side in the axial direction of the extension member 42 toward one side. An extension surface 48*a* of the extension part 48 inclined with respect to the axial direction is held by the plurality of engaging parts 46 of the engagement member 41.

In addition, a diameter of a portion where the outer diameter of the extension part 48 is the largest (hereinafter, referred to as a "maximum outer diameter") is set to be larger than the diameter of the space formed by the plurality of engaging parts 46 when the plurality of engaging parts 46 are in the natural state without being elastically deformed. Further, the maximum outer diameter of the extension part 48 is set to be larger than the outer diameter of the abutment piece 29 of the protector 26. In addition, first end portion in the axial direction of the extension part 48 is engaged with the engagement pieces 46*a* provided in the plurality of engaging parts 46 of the engagement member 41 in the extension member 42 after the puncture.

In addition, the first member 23 has the retaining member 43. The retaining member 43 is formed in a substantially disc shape. The retaining member 43 is fixed to the base part 31 so as to close an opening of the housing recess 36 on one side in the axial direction. A support hole 43*a* is opened in a central portion of the retaining member 43. The adjustment part 32, the support part 37, and the protector 26 are inserted through the support hole 43*a*. Further, the retaining member 43 supports the protector 26 so as to be movable along the axial direction of the support part 37.

In addition, the abutment piece 29 of the protector 26 abuts on the second end face in the axial direction of the retaining member 43 in the state before puncturing the skin with the needle tube 21. Accordingly, it is possible to inhibit the protector 26 biased by the biasing member 27 from falling out of the first member 23.

[Second Member]

Next, the second member 24 will be described. The second member 24 is formed in a tubular shape. First end portion in an axial direction of the second member 24 forms an insertion part 51 into which the base part 31 of the first member 23 is inserted, and the second end portion thereof forms a fitting part 52 into which the discharge part of the syringe 3 is fitted. A cylindrical hole 51*a* of the insertion part 51 is set to a size corresponding to the base part 31 of the first member 23.

A fixing piece 54 is provided on an outer peripheral surface of first end portion of the insertion part 51 in the axial direction of the second member 24. The fixing piece 54 is formed as a ring-shaped flange which is continuous to a distal end of the insertion part 51 and protrudes outward in the radial direction. The flat surface 35*b* of the connection piece 35 provided in the first member 23 abuts on and is fixed to the fixing piece 54. For example, an adhesive, ultrasonic welding, laser welding, a fixing screw, and the like can be used as a method of fixing the fixing piece 54 and the connection piece 35.

An outer diameter of the fitting part 52 is set to be smaller than an outer diameter of the insertion part 51. Further, a cylindrical hole 52*a* of the fitting part 52 is set to a size corresponding to the discharge part of the syringe 3 and has a diameter continuously decreasing toward the insertion part 51 side. In addition, a male screw part 52*b* configured to be screwed with the lock mechanism 12 of the syringe 3 is provided on an outer peripheral surface of the fitting part 52 (see FIG. 1). In addition, the elastic member 25 is disposed between the cylindrical hole 51*a* of the insertion part 51 and the cylindrical hole 52*a* of the fitting part 52.

[Elastic Member]

Next, the elastic member 25 will be described. The elastic member 25 is made of an elastically deformable member. Elastic materials, for example, various rubber materials, such as natural rubber, silicone rubber, and isobutylene rubber, various thermoplastic elastomers, such as a polyurethane type and a styrene type, or mixtures thereof can be used as a material of the elastic member 25.

The elastic member 25 is disposed inside the second member 24 and interposed between the first member 23 and the syringe 3. Further, a gap generated between the outer peripheral surface on the proximal end side of the needle tube 21 protruding from the first member 23 and the second member 24 is embedded by the elastic member 25. Further, the elastic member 25 is elastically deformed to come into liquid-tight close contact with the outer peripheral surface of the needle tube 21 when the discharge part of the syringe 3 is fitted into the second member 24. Accordingly, it is possible to inhibit the medicine filled in the syringe 3 from penetrating between the needle tube 21 and the elastic member 25 and leaking out toward the first member 23 side.

1-2. How to Use Medicine Injection Apparatus

Next, how to use the medicine injection apparatus 1 having the above-described configuration will be described with reference to FIGS. 1 to 4.

Figure 3:
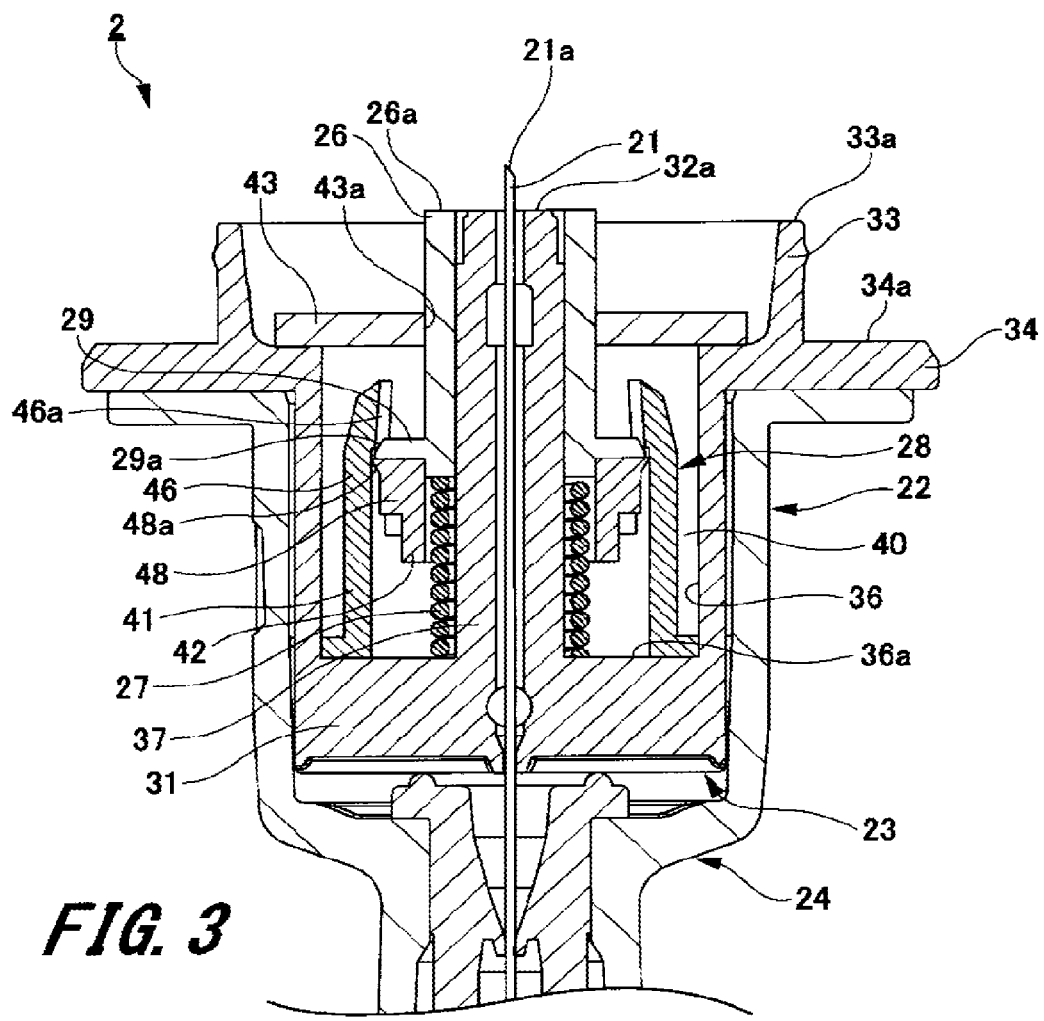
FIG. 3 is a cross-sectional view illustrating a state during puncture of the medicine injection apparatus according to the first embodiment of the present invention.
Figure 4:
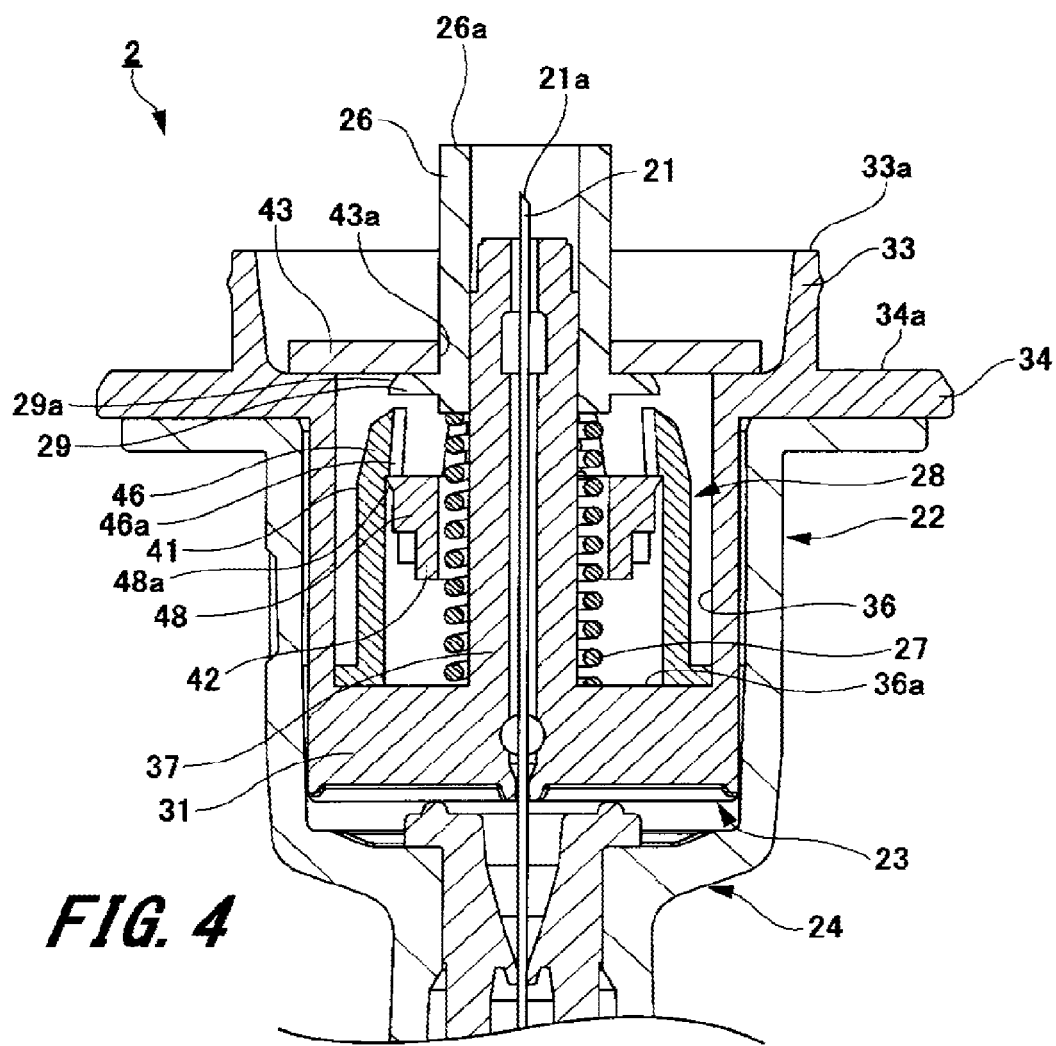
FIG. 4 is a cross-sectional view illustrating a state after puncture of the medicine injection apparatus according to the first embodiment of the present invention.

FIG. 3 is a cross-sectional view illustrating a main part of the medicine injection apparatus 1 during puncture, and FIG. 4 is a cross-sectional view illustrating the main part of the medicine injection apparatus 1 after puncture.

First, the syringe 3 is attached to the injection needle assembly 2 in advance as illustrated in FIGS. 1 and 2. Specifically, the discharge part of the syringe 3 is inserted into the fitting part 52 of the second member 24, and the lock mechanism 12 is screwed with the male screw part 52b. Accordingly, the attachment of the injection needle assembly 2 to the syringe 3 is completed.

At this time, the abutment piece 29 abuts on the retaining member 43 while the protector 26 is biased toward the first end side in the axial direction by the biasing member 27. Accordingly, it is possible to inhibit the protector 26 from falling out of the support part 37 of the first member 23. A position of the protector 26 at this time is set as a first position.

Further, the needle tip 21a of the needle tube 21 is covered with the protector 26 and is housed in the cylindrical hole of the protector 26. Accordingly, it is possible to inhibit the needle tip 21a of the needle tube 21 from puncturing against an intention of the user in the state before the puncture.

Next, the end face 33a of the stabilization part 33 is caused to oppose the skin. Accordingly, the needle tip 21a of the needle tube 21 is caused to oppose the skin to be punctured. Next, the medicine injection apparatus 1 is moved to be substantially perpendicular to the skin. Accordingly, a distal end face 26a of the protector 26 is pushed to the skin. Further, when the medicine injection apparatus 1 is pushed to the skin against the biasing force of the biasing member 27, the protector 26 moves in the axial direction of the support part 37, that is, along the axial direction of the needle tube 21. Accordingly, the needle protrusion surface 32a of the adjustment part 32 and the needle tip 21a side of the needle tube 21 protrude from a first end in the axial direction of the protector 26, that is, from the distal end face 26a, and the needle tip 21a side of the needle tube 21 is exposed. A position of the protector 26 at this time is set as a second position.

An inner peripheral surface of the protector 26 is supported by the outer peripheral surface of the support part 37, and the outer peripheral surface thereof is supported by the support hole 43a of the retaining member 43. Thus, the protector 26 can be smoothly moved without rattling.

When the protector 26 moves from one side to the other side in the axial direction of the support part 37, the extension member 42 is pressed by the abutment piece 29 of the protector 26 and moves together with the protector 26 from the one side to the other side in the axial direction of the support part 37. When the extension member 42 moves from one side to the other side in the axial direction of the support part 37, the plurality of engaging parts 46 that abut on the extension surface 48a of the extension part 48 are pressed by the extension part 48.

First end portion in an axial direction of the extension part 48 has an outer diameter continuously increasing from the other side in the axial direction of the extension member 42 toward one side. Thus, the plurality of engaging parts 46 are pressed outward in the radial direction. Further, the plurality of engaging parts 46 are elastically deformed so as to pivot about the proximal end portion on the cylindrical part 45 side, and an opening surrounded by the plurality of engaging parts 46 is pushed to spread outward in the radial direction. Accordingly, the abutment piece 29 of the protector 26 is inserted into the engagement member 41 together with the extension member 42 without being caught by the plurality of engaging parts 46 as illustrated in FIG. 3.

In addition, when the extension part 48 of the extension member 42 and the abutment piece 29 of the protector 26 pass over the engagement piece 46a of the plurality of engaging parts 46, the pressing force with respect to the plurality of engaging parts 46 is released. Further, the plurality of engaging parts 46 are restored to the original shape (natural state) by their own elasticity. At this time, the biasing member 27 is compressed by being elastically deformed between the abutment piece 29 of the protector 26 and the bottom surface 36a of the housing recess 36.

Further, the medicine injection apparatus 1 is moved to be substantially perpendicular to the skin, and the end face 33a of the stabilization part 33 is pushed to the skin at the same time of puncturing the skin with the needle tip 21a. At this time, the needle protrusion surface 32a can contact the skin to cause the skin to be deformed to be flat, and the needle tip 21a side of the needle tube 21 can be stuck into the skin by the protrusion length L.

Next, the end face 33a of the stabilization part 33 is pushed until the contact surface 34a of the guide part 34 comes into contact with the skin. Here, the length of the guide part height Y (see FIG. 2) is set such that the skin can be punctured by the needle tube 21 and the stabilization part 33 with the appropriate pressing force. Thus, a force pressing the skin by the stabilization part 33 becomes a predetermined value.

As a result, it is possible to cause the user to recognize the appropriate pressing force of the stabilization part 33, and to reliably position the needle tip 21a and the blade surface of the needle tube 21 in the skin upper layer portion. As the guide part 34 serves as a mark for recognition of the appropriate pressing force of the stabilization part 33 in this manner, the user can use the medicine injection apparatus 1 at ease.

In addition, the posture of the medicine injection apparatus 1 is stabilized as the stabilization part 33 comes into contact with the skin, and the needle tube 21 can be stuck straight to the skin. In addition, it is possible to inhibit shaking occurring in the needle tube 21 after puncture and to perform the stable administration of the medicine.

Further, there is a case where a needle tube having a very short protrusion length of, for example, about 0.5 mm is not stuck to the skin even by causing a needle tip to abut on the skin. However, the skin on the inner side of the stabilization part 33 is pulled as the skin pushed against the stabilization part 33 is pushed down in the vertical direction so that a state where a tensile force is applied to the skin is formed Thus, the skin hardly escapes with respect to the needle tip 21a of the needle tube 21. Therefore, it is also possible to obtain an effect of causing the needle tip 21a to be more easily stuck to the skin by providing the stabilization part 33.

In addition, when the above-described configuration is applied to a hypodermic injection apparatus which punctures a layer lower than a skin upper layer portion with a needle tube, a length of the needle tube puncturing the skin is longer than that of the injection needle assembly 2 which punctures the upper skin portion with the needle tube 21 according to the present embodiment, and thus, a length in the axial direction of the protector 26 increases. Thus, not only a length in the axial direction of the support part 37 supporting the protector 26, but also a movement distance of the protector 26 along the axial direction of the support part 37 becomes long. As a result, it is necessary to increase a length in the axial direction of the housing recess 36 provided in the base part 31 in the hypodermic injection apparatus, and there is a problem that the first member and the injection needle assembly become large.

On the other hand, since the injection needle assembly 2 according to the present embodiment is configured to puncture the skin upper layer portion with the needle tip 21a of the needle tube 21, the protrusion length L of the needle tube 21 is 0.5 to 3.0 mm, which is extremely short. Thus, it is possible to decrease the length in the axial direction of the protector 26, and further, it is also possible to significantly decrease the movement distance of the protector 26 along the axial direction of the support part 37. As a result, it is possible to inhibit the entire injection needle assembly 2 from becoming large even if the above-described configuration is applied to the injection needle assembly 2.

After puncturing the skin with the needle tip 21a side of the needle tube 21, the pusher member 4 (see FIG. 1) is pushed to move the gasket 13 to the discharge part side. Accordingly, the medicine filled in the liquid chamber 14 of the syringe 3 is pushed out from the discharge part and is injected from the needle tip 21a into the skin upper layer portion through the needle hole of the needle tube 21. At this time, it is possible to reduce the residual amount of the medicine since no space is formed between the distal end of the discharge part and the proximal end of the needle tube 21.

When the administration of the medicine is completed, the medicine injection apparatus 1 is separated from the skin, and the end face 33a of the stabilization part 33, the needle protrusion surface 32a, and the distal end face 26a of the protector 26 are moved away from the skin. At this time, the biasing member 27 is released from pressing from the skin via the protector 26. Then, the protector 26 is biased toward the needle tip 21a side of the needle tube 21 by a restoring force (biasing force) of the biasing member 27. Thus, the protector 26 is supported by the outer peripheral surface of the support part 37 and the support hole 43a of the retaining member 43 and moves toward one side from the other side in the axial direction of the support part 37 as illustrated in FIG. 4.

When the protector 26 moves toward one side from the other side in the axial direction of the support part 37, the inclined surface 29a of the abutment piece 29 abuts on the engagement pieces 46a of the plurality of engaging parts 46. The inclined surface 29a is formed into a tapered shape whose diameter continuously decreases from the other side to the one side in the axial direction. Thus, the plurality of engaging parts 46 are pressed outward in the radial direction, and the space surrounded by the plurality of engaging parts 46 is pushed to spread outward in the radial direction. Accordingly, the abutment piece 29 can pass the space among the plurality of engaging parts 46 without being caught by the plurality of engaging parts 46. In addition, when passing through the abutment piece 29, the pressing force with respect to the plurality of engaging parts 46 is released, and the plurality of engaging parts 46 are restored to the original shape (natural state) by their own elasticity.

Further, the abutment piece 29 abuts against the retaining member 43 so that the movement of the protector 26 in the axial direction is restricted. In addition, it is possible to inhibit the protector 26 from falling out of the support part 37 of the first member 23.

The protector 26 covers the periphery of the needle tip 21a of the needle tube 21, and the needle tube 21 is housed in the protector 26. That is, the protector 26 returns from the second position to the first position. Accordingly, it is possible to automatically move the protector 26 in accordance with the puncture operation and to easily cover the periphery of the needle tip 21a of the needle tube 21.

On the other hand, the maximum outer diameter of the extension part 48 is set to be larger than the outer diameter of the abutment piece 29 of the protector 26 in the extension member 42. Further, first end portion in the axial direction of the extension part 48 is engaged with the engagement pieces 46a of the plurality of engaging parts 46. Thus, the extension member 42 is detached from the protector 26 and remains inside the engagement member 41.

As the extension member 42 remains inside the engagement member 41, the space surrounded by the plurality of engaging parts 46 is not pushed to spread outward in the radial direction as the plurality of engaging parts 46 are pressed outward in the radial direction. In addition, the abutment piece 29 abuts on the plurality of engaging parts 46 of the engagement member 41 when the protector 26 is pressed from one side toward the other side in the axial direction of the support part 37. Thus, the protector 26 after puncture is restricted from moving from one side to the other side in the axial direction. Accordingly, it is possible to inhibit the needle tip 21a of the needle tube 21 after puncture from protruding again from the distal end face 26a of the protector 26. As a result, it is possible to maintain the needle tip 21a of the needle tube 21 after use in a safe state, and it is possible to inhibit the needle tip 21a of the needle tube 21 after use from puncturing against the intention of the user.

Further, since the needle tip 21a of the needle tube 21 after use is covered by the protector 26, it is possible to inhibit scattering of blood adhering to the needle tip 21a, and it is also possible to inhibit infection caused by the blood.

2. Second Embodiment

Next, a medicine injection apparatus according to a second embodiment will be described with reference to FIGS. 5 to 7.

Figure 5:
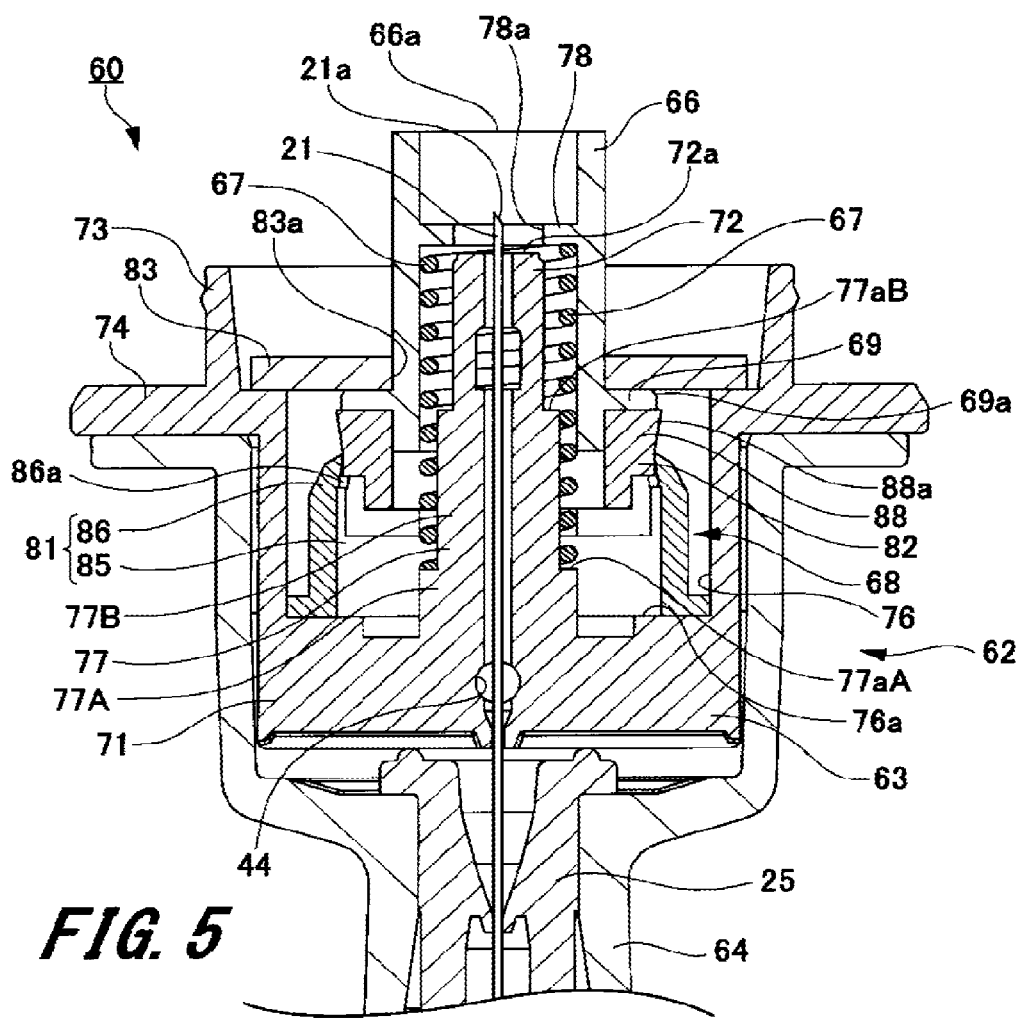
FIG. 5 is a cross-sectional view illustrating a medicine injection apparatus according to a second embodiment of the present invention.
Figure 6:
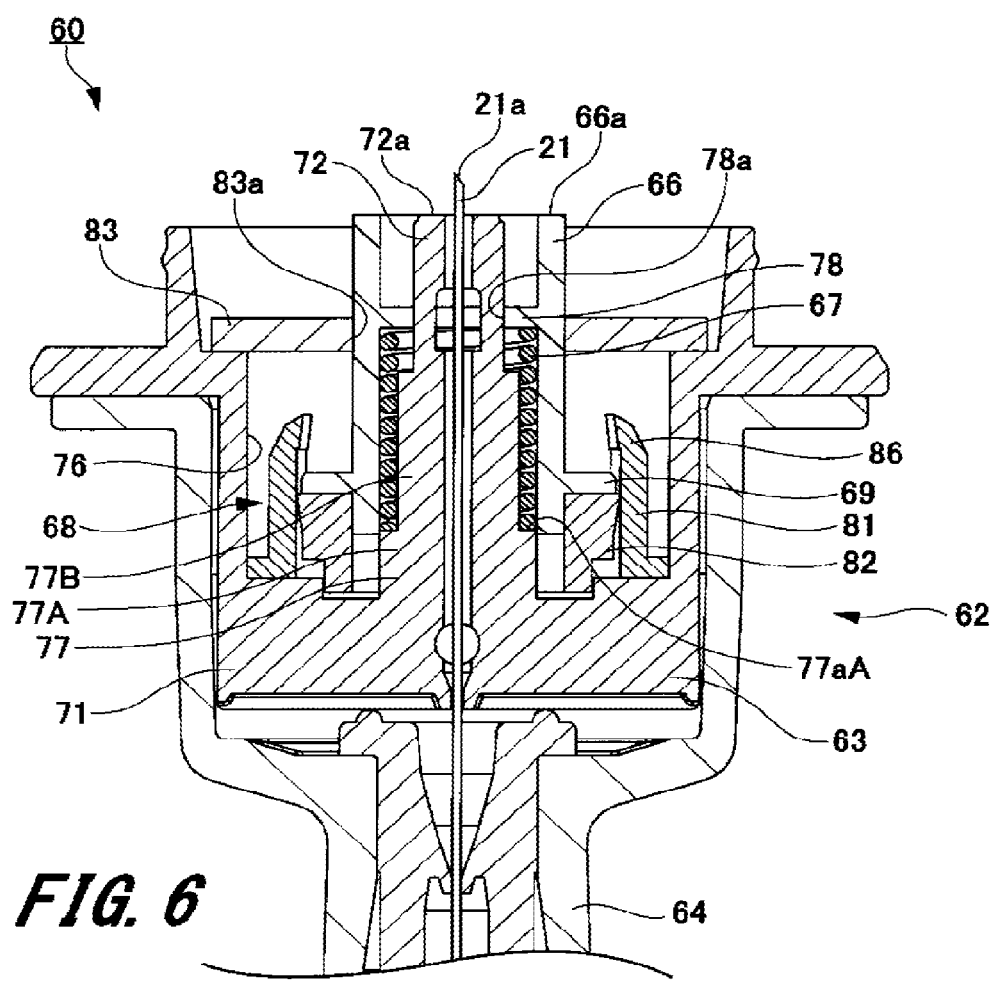
FIG. 6 is a cross-sectional view illustrating a state during puncture of the medicine injection apparatus according to the second embodiment of the present invention.
Figure 7:
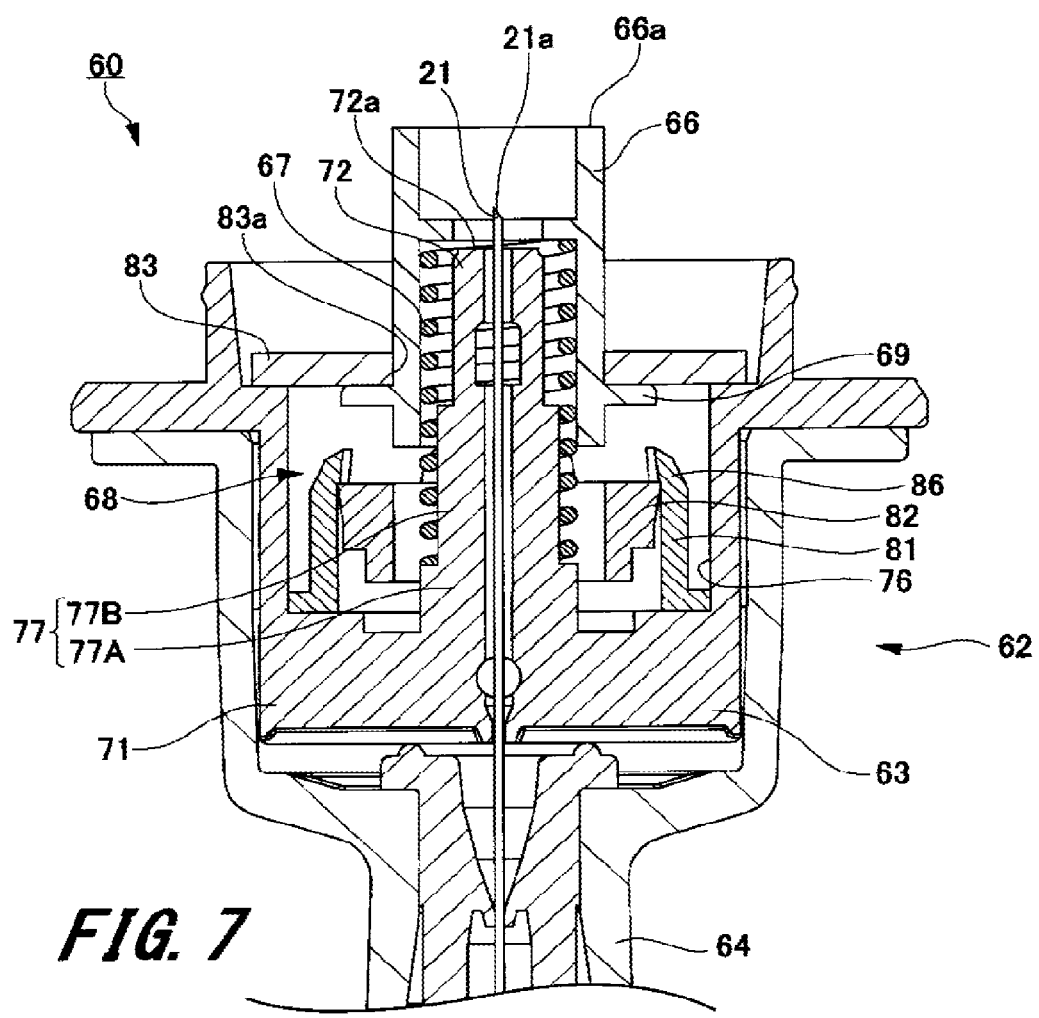
FIG. 7 is a cross-sectional view illustrating a state after puncture of the medicine injection apparatus according to the second embodiment of the present invention.

FIG. 5 is a cross-sectional view illustrating a state before puncture, FIG. 6 is a sectional view illustrating a state during puncture, and FIG. 7 is a sectional view illustrating a state after puncture.

The medicine injection apparatus according to the second embodiment is different from the medicine injection apparatus 1 according to the first embodiment in terms of configurations of a first member, a biasing member, and a protector in an injection needle assembly. Thus, the first member, the biasing member, and the protector will be mainly described here. Common parts to those of the injection needle assembly 2 according to the first embodiment will be denoted by the same reference signs, and the redundant description thereof will be omitted.

As illustrated in FIG. 5, an injection needle assembly 60 includes the hollow needle tube 21 and a needle hub 62 which holds the needle tube 21. The needle hub 62 includes a first member 63, a second member 64 into which the discharge part of the syringe 3 is fitted, the elastic member 25, a protector 66, a biasing member 67, and a restriction mechanism 68.

The first member 63 includes a base part 71, an adjustment part 72, a stabilization part 73, a guide part 74, and a support part 77. The base part 71 is formed in a substantially columnar shape. A housing recess 76 is formed in the base part 71. The entire first end face in an axial direction of the base part 71 is opened. The housing recess 76 is formed to be recessed in a substantially columnar shape from a first end to the second end in an axial direction of the base part 71. A support part 77 is formed in the housing recess 76.

The support part 77 is provided at a central portion of a bottom surface 76a of the housing recess 76 and protrudes from the bottom surface 76a of the housing recess 76 in the axial direction of the base part 71. The support part 77 has a first pillar 77A and a second pillar 77B. The first pillar 77A and the second pillar 77B are formed in a substantially columnar shape.

The first pillar 77A protrudes in the axial direction of the base part 71 from the bottom surface 76a of the housing recess 76. The second pillar 77B is provided at a central portion of a first end face 77aA in an axial direction of the first pillar 77A and protrudes in the axial direction of the base part 71. An axial center of the first pillar 77A and an axial center of the second pillar 77B coincide with each other. An outer diameter of the second pillar 77B is set to be smaller than an outer diameter of the first pillar 77A.

In addition, the adjustment part 72 is provided on a first end face 77aB in an axial direction face of the second pillar 77B. The adjustment part 72 is provided at a central portion of the first end face 77aB of the second pillar 77B. Further, an axial center of the adjustment part 72 coincides with the axial centers of the first pillar 77A and the second pillar 77B.

Next, the protector 66 will be described. The protector 66 is formed in a tubular shape, and covers the second pillar 77B and the periphery of the adjustment part 72 through which the needle tube 21 passes and the needle tip 21a of the needle tube 21 in the state before puncturing the skin with the needle tube 21. The protector 66 is supported by a retaining member 83 and the support part 37 so as to be movable in the axial direction.

The protector 66 is provided with an abutment piece 69 and a spring abutment part 78. The abutment piece 69 is provided on an outer peripheral surface of the protector 66 on the second end side in the axial direction. In addition, an inclined surface 69a is formed on the abutment piece 69. The spring abutment part 78 is disposed at first end portion in the axial direction of the protector 66.

The spring abutment part 78 is an inner flange that is continuously provided in the circumferential direction of an inner wall of the protector 66 and protrudes inward in the radial direction of the protector 66. An insertion hole 78a through which the adjustment part 72 and the needle tip 21a of the needle tube 21 are inserted is provided on the inner side in the radial direction of the spring abutment part 78.

The biasing member 67 is disposed so as to cover the second pillar 77B of the support part 77 and the periphery of the adjustment part 72 in a cylindrical hole of the protector 66. First end portion in an axial direction of the biasing member 67 abuts on the spring abutment part 78, and the second end portion in the axial direction of the biasing member 67 abuts on the first end face 77aA of the first pillar 77A. Further, the biasing member 67 biases the protector 66 toward one side in the axial direction, that is, the needle tip 21a side of the needle tube 21.

Next, the restriction mechanism 68 will be described. The restriction mechanism 68 has an engagement member 81 and an extension member 82, which is similar to the restriction mechanism 28 according to the first embodiment.

The engagement member 81 has a cylindrical part 85 formed in a substantially cylindrical shape and a plurality of engaging parts 86. The engagement member 81 is disposed in the housing recess 76. The plurality of engaging parts 86 are provided with engagement pieces 86a, respectively.

In addition, the extension member 82 is formed in a substantially tubular shape, and is detachably attached to an outer peripheral portion of the protector 66 on the other side in the axial direction with respect to the abutment piece 69. In addition, the extension member 42 is provided with an extension part 88. An extension surface 88a that is inclined with respect to the axial direction is formed in the extension part 88.

In addition, the first member 63 has the retaining member 83. The retaining member 83 is formed in a substantially disc shape, and a support hole 83a is opened in a central portion thereof. The adjustment part 72, the second pillar 77B of the support part 77, and the protector 66 are inserted through the support hole 83a. Further, the retaining member 83 supports the protector 66 so as to be movable along the axial direction of the support part 77.

Next, an operation of the protector 66 of the injection needle assembly 60 according to the second embodiment having the above-described configuration will be described.

As illustrated in FIG. 5, the abutment piece 69 abuts on the retaining member 83 in the state before puncture. At this time, the protector 66 covers the second pillar 77B and the periphery of the adjustment part 72 through which the needle tube 21 passes and the needle tip 21a of the needle tube 21. Accordingly, it is possible to inhibit erroneous puncture of the needle tip 21a of the needle tube 21 before puncturing the skin with the needle tip 21a side of the needle tube 21.

Next, when the distal end face 66a of the protector 66 is pushed to the skin against the biasing force of the biasing member 67, the extension member 82 and the abutment piece 69 of the protector 66 are inserted into the engagement member 81. Further, the protector 66 is supported by the support hole 83a of the retaining member 83, and the protector 66 moves along the support part 77. Further, the needle protrusion surface 72a of the adjustment part 72 and the needle tip 21a of the needle tube 21 protrude from the insertion hole 78a of the protector 66 as illustrated in FIG. 6.

At this time, the biasing member 67 is compressed by being elastically deformed between the spring abutment part 78 of the protector 66 and the first end face 77aA of the first pillar 77A.

Next, when the injection needle assembly is separated from the distal end face 66a of the protector 66, the biasing member 67 is released from pressing from the skin via the protector 66. Then, the protector 66 is biased toward the needle tip 21a side of the needle tube 21 by a restoring force (biasing force) of the biasing member 67.

As illustrated in FIG. 7, the abutment piece 69 pushes the plurality of engaging parts 86 to spread outward in the radial direction, and further, passes a space among the plurality of engaging parts 86. In addition, the abutment piece 69 abuts on the retaining member 83. Then, the protector 66 covers the periphery of the needle tip 21a of the needle tube 21, and the needle tube 21 is housed in the protector 66. At this time, the extension member 82 remains inside the engagement member 81.

Since the other configurations are the same as those of the injection needle assembly 2 according to the first embodiment, the description thereof will be omitted. Even with the injection needle assembly 60 configured as above, it is possible to obtain the same action and effect as those of the injection needle assembly 2 according to the first embodiment described above.

In addition, the biasing member 67 is housed in the cylindrical hole of the protector 66 in the injection needle assembly 60 according to the second embodiment. Thus, the biasing member 67 is disposed closer to the needle tip 21a side of the needle tube 21 than the biasing member 27 of the injection needle assembly 2 according to the first embodiment. Accordingly, it is possible to set a length in an axial direction of the housing recess 76, formed in the base part 71, to be shorter than the length in the axial direction of the housing recess 36 according to the first embodiment, and it is possible to make the first member 63 smaller than the first member 23 according to the first embodiment.

Further, it is possible to set a length in an axial direction of the engagement member 81, housed in the housing recess 76, to be shorter than the length in the axial direction of the engagement member 41 according to the first embodiment. As a result, it is possible to obtain the reduction in size of the injection needle assembly 60.

Further, it is possible to cause the biasing member 67 to be separated from the engagement member 81 and the extension member 82 of the restriction mechanism 68 when the biasing member 67 to be elastically deformed is housed in the cylindrical hole of the protector 66 and disposed on a distal end side in the axial direction of the first member 63. Accordingly, it is possible to inhibit the respective members from interfering with each other when the biasing member 67 is elastically deformed, when extension member 82 moves, when the protector 66 moves, and when the plurality of engaging parts 86 of the engagement member 81 are elastically deformed. As a result, it is possible to smoothly perform the movement operation of the protector 66.

As above, the embodiments of the medicine injection apparatus and the injection needle assembly according to the present invention have been described including the action and effect thereof. However, the medicine injection apparatus and the injection needle assembly according to the present invention are not limited to the above-described embodiments, and various modifications can be made within a scope not departing from a gist of the invention described in the claims.

Although the example in which the luer lock part is provided as the lock mechanism 12 has been described the above-described embodiments, the present invention is not limited thereto. A male screw part may be provided in the discharge part to be screwed with a female screw part provided in the cylindrical hole of the second member 24 of the injection needle assembly 2.

REFERENCE NUMERAL LIST

1 . . . medicine injection apparatus,
2, 60 . . . injection needle assembly,
3 . . . syringe,
4 . . . pusher member,
21 . . . needle tube,
21a . . . needle tip,
22, 62 . . . needle hub,
23, 63 . . . first member,
24, 64 . . . second member,
26, 66 . . . protector,
26a, 66a . . . distal end face,
27, 67 . . . biasing member,
28 . . . restriction mechanism,
29, 69 . . . abutment piece,
29a, 69a . . . inclined surface,
31, 71 . . . base part,
32, 72 . . . adjustment part,
32a, 72a . . . needle protrusion surface,
33, 73 . . . stabilization part,
33a . . . end face,
34, 74 . . . guide part,
34a . . . contact surface,
36, 76 . . . housing recess,
36a, 76a . . . bottom surface,
37 . . . support part,
40 . . . space,
41, 81 . . . engagement member,
42, 82 . . . extension member,
43, 83 . . . retaining member,
43a, 83a . . . support hole,
45, 85 . . . cylindrical part,
46, 86 . . . engaging part,
46a, 86a . . . engagement piece,
48, 88 . . . extension part,
48a, 88a . . . extension surface,
77A . . . first pillar,
77aA, 77aB . . . first end face,
77B . . . second pillar,
78 . . . spring abutment part,
78a . . . insertion hole

What is claimed is:

1. An injection needle assembly comprising:
a needle tube having a needle tip configured to puncture a living body;
a needle hub holding the needle tube;
a protector movable between a first position at which the needle tip of the needle tube is covered and a second position at which the needle tip of the needle tube is exposed, the protector comprising an abutment piece;
a biasing member configured to bias the protector toward the needle tip of the needle tube along an axial direction of the needle tube;
a retaining member that supports the protector such that the protector is movable along the axial direction of the needle tube, wherein the abutment piece abuts on the retaining member when the protector is moved to the first position; and
a restriction mechanism configured such that, after the protector has moved from the first position to the second position and has further returned from the second position to the first position, the restriction mechanism restricts the protector from moving from the first position to the second position again,
wherein the restriction mechanism comprises:
an engagement member having an engaging part that is elastically deformable in a radially outward direction of the needle tube, and
an extension member that is detachably attached to the protector, the extension member comprising an extension part that pushes an opening formed by the engaging part to spread in the radially outward direction when the protector moves from the first position to the second position, wherein the extension member passes through the engaging part and is inserted into the engagement member together with the abutment piece when the protector moves from the first position to the second position, and wherein the extension member is detached from the protector and engaged with the engaging part when the protector returns to the first position from the second position.

2. The injection needle assembly according to claim 1, wherein:
the needle hub is formed with a housing recess that is open on a needle tip side of the needle tube, and
the restriction mechanism is housed in the housing recess.

3. The injection needle assembly according to claim 1, wherein:
the biasing member is on a needle tip side of the restriction mechanism in the axial direction of the needle tube.

4. The injection needle assembly according to claim 1, further comprising:
an adjustment part that is provided around the needle tube, is configured to come into contact with skin when the needle tube punctures the living body, and has a needle protrusion surface from which the needle tip of the needle tube protrudes,
wherein the protector covers a periphery of the adjustment part when the protector is at the first position.

5. The injection needle assembly according to claim 4, further comprising:
a stabilization part that extends from the needle hub, is disposed so as to cover the needle tube and a periphery of the protector, and has an end face configured to come into contact with the skin when the needle tube punctures the living body; and
a guide part that is formed in a flange shape protruding in a radial direction from a periphery of the stabilization part so as to be substantially perpendicular to an outer side of the stabilization part in a radial direction.

6. A medicine injection apparatus comprising:
an injection needle assembly comprising a needle tube having a needle tip configured to puncture a living body; and
a syringe that is detachably attached to the injection needle assembly,
wherein the injection needle assembly comprises:
a needle hub holding the needle tube,
a protector movable between a first position at which the needle tip of the needle tube is covered and a second position at which the needle tip of the needle tube is exposed, the protector comprising an abutment piece,
a biasing member configured to bias the protector toward the needle tip of the needle tube along an axial direction of the needle tube,
a retaining member that supports the protector such that the protector is movable along the axial direction of the needle tube, wherein the abutment piece abuts on the retaining member when the protector is moved to the first position, and
a restriction mechanism configured such that, after the protector has moved from the first position to the second position and has further returned from the second position to the first position, the restriction mechanism restricts the protector from moving from the first position to the second position again
wherein the restriction mechanism comprises:
an engagement member having an engaging part that is elastically deformable in a radially outward direction of the needle tube, and
an extension member that is detachably attached to the protector, the extension member comprising an extension part that pushes an opening formed by the engaging part to spread in the radially outward direction when the protector moves from the first position to the second position,
wherein the extension member passes through the engaging part and is inserted into the engagement member together with the abutment piece when the protector moves from the first position to the second position, and
wherein the extension member is detached from the protector and engaged with the engaging part when the protector returns to the first position from the second position.

* * * * *